United States Patent
Braga (10) Patent No.: US 9,108,030 B2
(45) Date of Patent: Aug. 18, 2015

(54) FLUID DELIVERY CATHETER WITH PRESSURE-ACTUATING NEEDLE DEPLOYMENT AND RETRACTION

(71) Applicant: Covidien LP, Mansfield, MA (US)

(72) Inventor: Richard M. Braga, North Easton, MA (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 13/826,237

(22) Filed: Mar. 14, 2013

(65) Prior Publication Data

US 2014/0276621 A1 Sep. 18, 2014

(51) Int. Cl.
*A61M 37/00* (2006.01)
*A61M 25/10* (2013.01)
*A61M 25/00* (2006.01)

(52) U.S. Cl.
CPC ....... *A61M 37/0015* (2013.01); *A61M 25/0084* (2013.01); *A61M 2025/006* (2013.01); *A61M 2025/0085* (2013.01); *A61M 2025/0089* (2013.01); *A61M 2025/0093* (2013.01); *A61M 2025/1086* (2013.01)

(58) Field of Classification Search
CPC .......... A61M 25/0084; A61M 2025/0085; A61M 2025/0087; A61M 2025/1086; A61M 2025/006; A61M 2025/1088; A61M 2025/1031; A61M 2025/09116; A61M 37/0015; A61M 2037/0023; A61M 2037/003; A61M 2037/0038
USPC .......... 604/103.01, 103.06, 103.08, 173, 604/101.01, 101.02, 103.02, 264, 271, 272
See application file for complete search history.

(56) References Cited

U.S. PATENT DOCUMENTS

| | | | |
|---|---|---|---|
| 5,196,024 A | 3/1993 | Barath | |
| 5,242,397 A | 9/1993 | Barath et al. | |
| 5,354,279 A | 10/1994 | Hofling | |
| 5,423,851 A | 6/1995 | Samuels | |
| 5,693,029 A | 12/1997 | Leonhardt | |
| 5,746,716 A | 5/1998 | Vigil et al. | |
| 5,906,599 A | 5/1999 | Kaldany | |
| 5,954,740 A * | 9/1999 | Ravenscroft et al. | 606/194 |
| 6,102,904 A | 8/2000 | Vigil et al. | |
| 6,547,767 B1 * | 4/2003 | Moein | 604/264 |
| 6,547,803 B2 | 4/2003 | Seward et al. | |
| 7,008,411 B1 | 3/2006 | Mandrusov et al. | |
| 7,338,468 B2 | 3/2008 | Freyman | |
| 7,837,670 B2 | 11/2010 | Barath | |
| 8,016,786 B2 | 9/2011 | Seward et al. | |
| 2002/0161389 A1 * | 10/2002 | Boyle et al. | 606/200 |
| 2004/0044308 A1 | 3/2004 | Naimark et al. | |
| 2004/0158280 A1 * | 8/2004 | Morris et al. | 606/200 |
| 2005/0273049 A1 * | 12/2005 | Krulevitch et al. | 604/101.02 |
| 2005/0273075 A1 * | 12/2005 | Krulevitch et al. | 604/509 |

(Continued)

OTHER PUBLICATIONS

Extended Search Report from counterpart European Patent Application No. 14153643.3, dated Feb. 2, 2015, 7 pp.

*Primary Examiner* — William Frehe
(74) *Attorney, Agent, or Firm* — Thomas M. Johnston, Esq.

(57) ABSTRACT

A fluid delivery catheter that uses micro-needles for fluid delivery though a vessel wall. The catheter may provide fluid delivery therapy for various procedures, such as, for example, delivery of tumescent fluid or renal denervation. The catheter includes an elongate member with deployable and retractable needles disposed about a distal end of the elongate member. The needles may be disposed radially about the distal end and/or along a length of the distal end.

9 Claims, 8 Drawing Sheets

(56) References Cited

U.S. PATENT DOCUMENTS

| | | | |
|---|---|---|---|
| 2009/0240270 A1 | 9/2009 | Schneider et al. | |
| 2009/0270906 A1* | 10/2009 | Hossainy | 606/194 |
| 2011/0125140 A1* | 5/2011 | Beck et al. | 606/14 |
| 2011/0208221 A1 | 8/2011 | Gennrich et al. | |
| 2012/0053485 A1* | 3/2012 | Bloom | 600/567 |
| 2012/0109276 A1* | 5/2012 | Diener et al. | 623/1.11 |
| 2014/0276406 A1* | 9/2014 | Campbell et al. | 604/103.02 |

* cited by examiner

FLUID DELIVERY CATHETER WITH PRESSURE-ACTUATING NEEDLE DEPLOYMENT AND RETRACTION

TECHNICAL FIELD

The present embodiments relate generally to therapy for hollow anatomical structures, and more specifically to a fluid delivery catheter with pressure-actuated needle deployment and retraction.

BACKGROUND

Many medical procedures are conducted within or around a body vessel, such as a blood vessel. Such procedures often require the delivery of a therapeutic fluid or agent to a length of the vessel or around the vessel. For example, treatment of varicose veins may require the delivery of a tumescent fluid around a length of a blood vessel to compress the blood vessel around and onto a therapeutic device within the blood vessel lumen. Similarly, to treat varicose veins, a sclerosant may be injected along the length of a blood vessel to irritate and eventually close the blood vessel.

In other procedures, a drug may be delivered along the length of a vessel to affect various tissue in and around the vessel. For example, in renal denervation, which is a procedure to lower blood pressure, a drug may be delivered to the renal artery to affect the nerves in or around the vascular wall.

Delivery of the therapeutic fluid along a length of the vessel is often an issue. For example, therapeutic fluid may be delivered subcutaneously around the vessel, such as injecting tumescent fluid around a vein for varicose vein treatment, which requires multiple injections along the length of the vein. Injection of a therapeutic fluid from within the vessel lumen often requires moving a single needle along and around the vessel lumen to provide enough of the therapeutic fluid. Both are time consuming, requiring significant manipulation and multiple injections at multiple sites. Therefore, a more effective device to inject therapeutic fluid along a length or around a body vessel is needed.

SUMMARY

The various embodiments of the present apparatus and methods have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

The present disclosure provides a fluid delivery catheter with pressure-actuated needle deployment and retraction that enables multiple injections along and/or around a hollow anatomical structure simultaneously.

In general, in one aspect, the implementation of the disclosure features an apparatus for delivery of a fluid at a treatment site. The apparatus includes an elongate catheter having an outer sleeve defining a treatment length at or near a distal end of the catheter. The outer sleeve defines a plurality of spaced apertures and an outer sleeve lumen. The apparatus also includes a flexible inner lining disposed within the outer sleeve lumen and defines a plurality of independently pressure-deformable portions and a lining lumen. Each of the plurality of pressure deformable portions is generally aligned with one of the plurality of spaced apertures. A plurality of micro-needles are secured to the pressure-deformable portions and are in fluid communication with the lining lumen. The pressure-deformable portions and the micro-needles are recessed beneath an outer surface of the outer sleeve in an at-rest configuration, and the pressure-deformable portions are deformable to an extended position in which at least a portion of the micro-needles protrude above the outer surface of the outer sleeve.

One or more of the following features may be included. The pressure-deformable portions may be deformed to the extended position by a pressurized fluid delivered into the lining lumen. Alternatively, or additionally, the pressure-deformable portions may be deformed to the extended position by an elongate wire that includes annular grooves and/or longitudinal grooves. Further, the pressure-deformable portions may be biased radially inward.

The pressure-deformable portions may be spaced from one another along a longitudinal axis of the treatment length and/or about a circumference of the treatment length. In embodiments, the spacing and position of the pressure-deformable portions trace a helix about the treatment length.

Further, the pressure-deformable portions may be shaped as a conical frustum. Each of the micro-needles may be secured to a base of each of the frustums. Also, a distal end of the catheter may be closed.

In general, in another aspect, the implementation of the disclosure features an apparatus for delivery of a fluid at a treatment site that includes an elongate catheter having an outer sleeve defining a treatment length at or near a distal end of the catheter. The outer sleeve defines a plurality of spaced apertures and an outer sleeve lumen. A flexible inner lining is disposed within the outer sleeve lumen and defines a plurality of independently pressure-deformable portions and a lining lumen, wherein each of the pressure deformable portions are shaped as a conical frustum that is biased radially inward and positioned to generally aligned with one of the plurality of spaced apertures. A plurality of micro-needles are secured to a base of the frustum of the pressure-deformable portions and are in fluid communication with the lining lumen. The pressure-deformable portions and the micro-needles are recessed beneath an outer surface of the outer sleeve in an at-rest configuration, and the pressure-deformable portions are deformable to an extended position in which at least a portion of the micro-needles protrude above the outer surface of the outer sleeve.

One or more of the following features may be included. The pressure-deformable portions may be deformed to the extended position by a pressurized fluid delivered into the lining lumen. Alternatively, or in addition, the pressure-deformable portions may be deformed to the extended position by an elongate wire that includes annular grooves and/or longitudinal grooves.

In general, in another aspect, the implementation of the disclosure features a method of delivering a fluid at a treatment site within a hollow anatomical structure (HAS). The method includes positioning a treatment length of an elongate catheter at the treatment site. The treatment length includes an outer sleeve defining a plurality of spaced apertures and a sleeve lumen. The treatment length further includes a flexible inner lining defining a plurality of independently pressure-deformable portions and a lining lumen disposed within the sleeve lumen. Each of the plurality of pressure deformable portions are generally aligned with one of the plurality of spaced apertures. The treatment length further includes a plurality of micro-needles, each micro-needle being secured to one of the pressure-deformable portions and is in fluid communication with the lining lumen. The pressure-deformable portions and the micro-needles are recessed beneath an outer surface of the outer sleeve in an at-rest state. The method further includes deforming the pressure-deformable portions to an extended position in which at least a portion of the micro-needles protrude above the outer surface of the outer sleeve to penetrate a wall of the HAS. The method also includes delivering the fluid under pressure into the lining lumen, through needle lumens of the micro-needles and into the HAS wall.

One or more of the following features may also be included. The pressure-deformable portions may be deformed to the extended position by the pressurized fluid delivered into the lining lumen. Alternatively, or in addition, the pressure-deformable portions may be deformed to the extended position by an elongate wire that includes annular grooves and/or longitudinal grooves.

The therapeutic fluid flows into the HAS wall at a plurality of locations simultaneously that correspond to positions of the plurality of micro-needles.

Further, ceasing delivery of the therapeutic fluid may cause the pressure-deformable portions to retract radially inward such that the micro-needles are again recessed beneath the outer surface of the outer sleeve to enable removal of the elongate catheter.

The pressure-deformable portions may be spaced from one another along a longitudinal axis of the treatment length and/or about a circumference of the treatment length. In embodiments, the pressure-deformable portions trace a helix about the treatment length.

In various methods, tumescent anesthesia may be injected to the treatment site prior to delivering the therapeutic fluid under pressure.

The disclosure may be implemented to realize one or more of the following advantages. The elongate catheter can deliver fluid to multiple injection sites simultaneously with minimal manipulation. The elongate catheter may be used to inject various fluids, such as anesthesia, sclerosant agents, or medicants. The retractable needles enable a reduced diameter of the elongate catheter for delivery into various hollow anatomical structures. The micro-needles may be sized to inject fluid into the hollow anatomical structure or to tissue outside the hollow anatomical structure. Other features and advantages of the invention are apparent from the following description.

BRIEF DESCRIPTION OF THE DRAWINGS

The present embodiments now will be discussed in detail with an emphasis on highlighting the advantageous features. These embodiments are for illustrative purposes only. These drawings include the following figures, in which like numerals indicate like parts.

DETAILED DESCRIPTION

The following detailed description describes the present embodiments with reference to the Figures. In the Figures, reference numbers label elements of the present embodiments. These reference numbers are reproduced below in connection with the discussion of the corresponding Figures' features. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece.

The present embodiments include a fluid delivery catheter that uses micro-needles for fluid delivery though a vessel wall. The catheter may be configured to provide fluid delivery therapy for various procedures, such as, for example, delivery of tumescent fluid or renal denervation. One advantage of the present catheter is its ability to efficiently and simultaneously deliver fluid therapy from within a vessel lumen to the vessel wall or just outside the vessel wall via multiple targeted delivery areas. The catheter includes an elongate member with deployable and retractable needles disposed about a distal end of the elongate member. The needles may be disposed radially about the distal end and/or along a length of the distal end.

Figure 1:
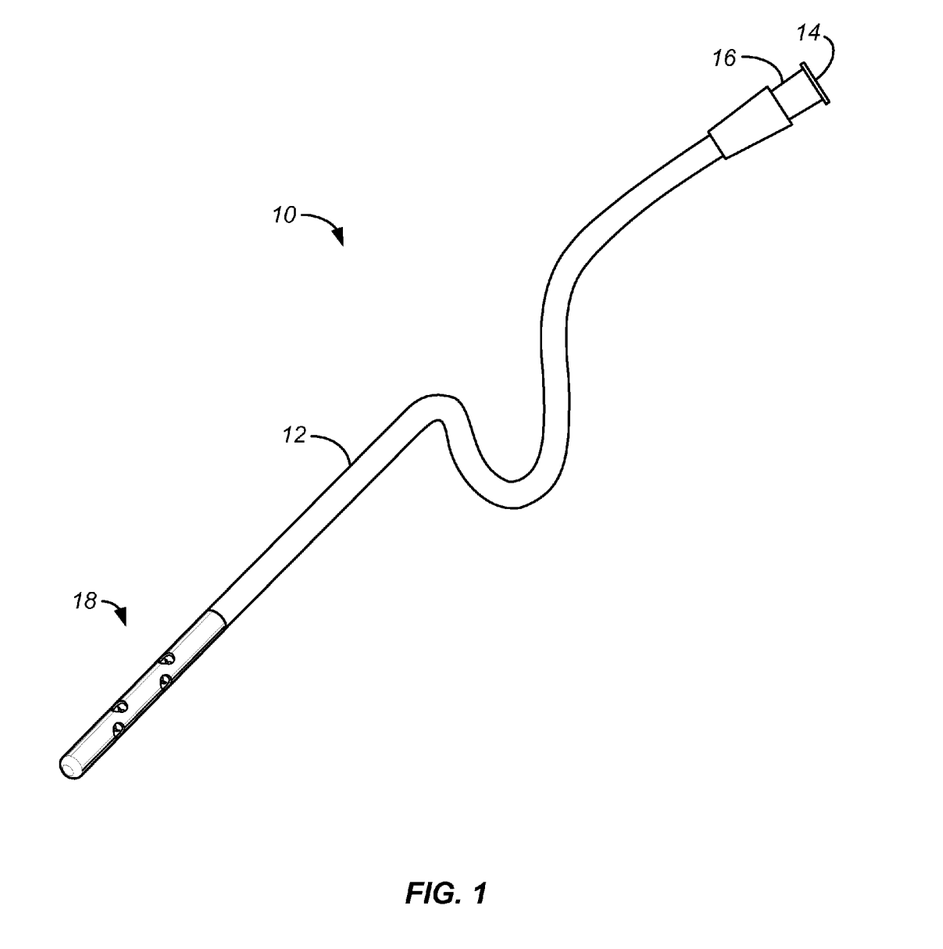
FIG. 1 is a side perspective view of a fluid delivery catheter according to the present embodiments.

FIG. 1 illustrates one example embodiment of the present fluid delivery catheter 10. The catheter 10 comprises a flexible elongate member 12 defining an internal lumen (not shown). A proximal end 14 of the catheter 10 may include a female coupler 16 configured to receive a source of therapeutic fluid (not shown). For example, the female coupler 16 may comprise a female luer lock fitting configured to receive a syringe having a corresponding male luer lock fitting.

The catheter 10 is preferably sized and configured to be advanced through a patient's target vessel lumen, such as the vasculature, from an access site on the body to a treatment site within the vasculature. Example dimensions for the catheter 10 include an outside diameter of approximately 8 French, or in the range of 4 French to 12 French, and a length in the range of 50 cm-200 cm, or about 80 cm, or about 120 cm. Material(s) from which the catheter 10 is constructed is preferably rigid enough to enable it to be pushed distally through the vasculature, but flexible enough to enable navigation of tortuous vasculature. Example materials for the catheter 10 include polyurethane, polyether block amide (PEBAX™), or any lubricious and/or hydrophilic polymer such as nylon, polyethylene or EVA. One suitable composition may comprise 39% Pebax 63D, 39% Pebax 72D, 20% $BaSO_4$, and 2% $TiO_2$.

With continued reference to FIG. 1, a distal portion of the catheter 10 comprises a treatment length 18. The treatment length 18 may be a unitary extension of the catheter 10, or may be a discrete portion secured to the catheter 10. The treatment length 18 is illustrated in the detail views of FIGS. 2-5.

Figure 2:
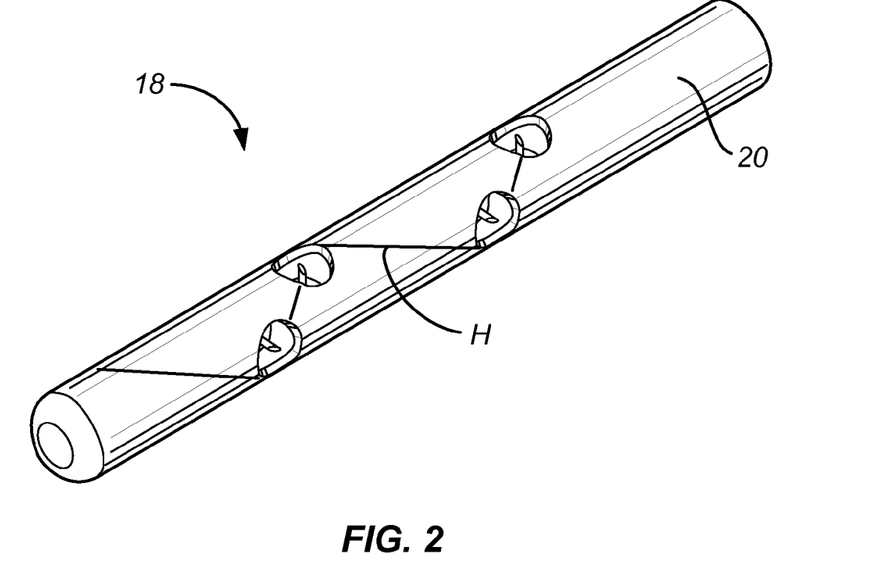
FIG. 2 is a detail view of the portion of the fluid delivery catheter of FIG. 1 indicated by the circle 1-1, showing the micro-needles in a retracted position.
Figure 3:
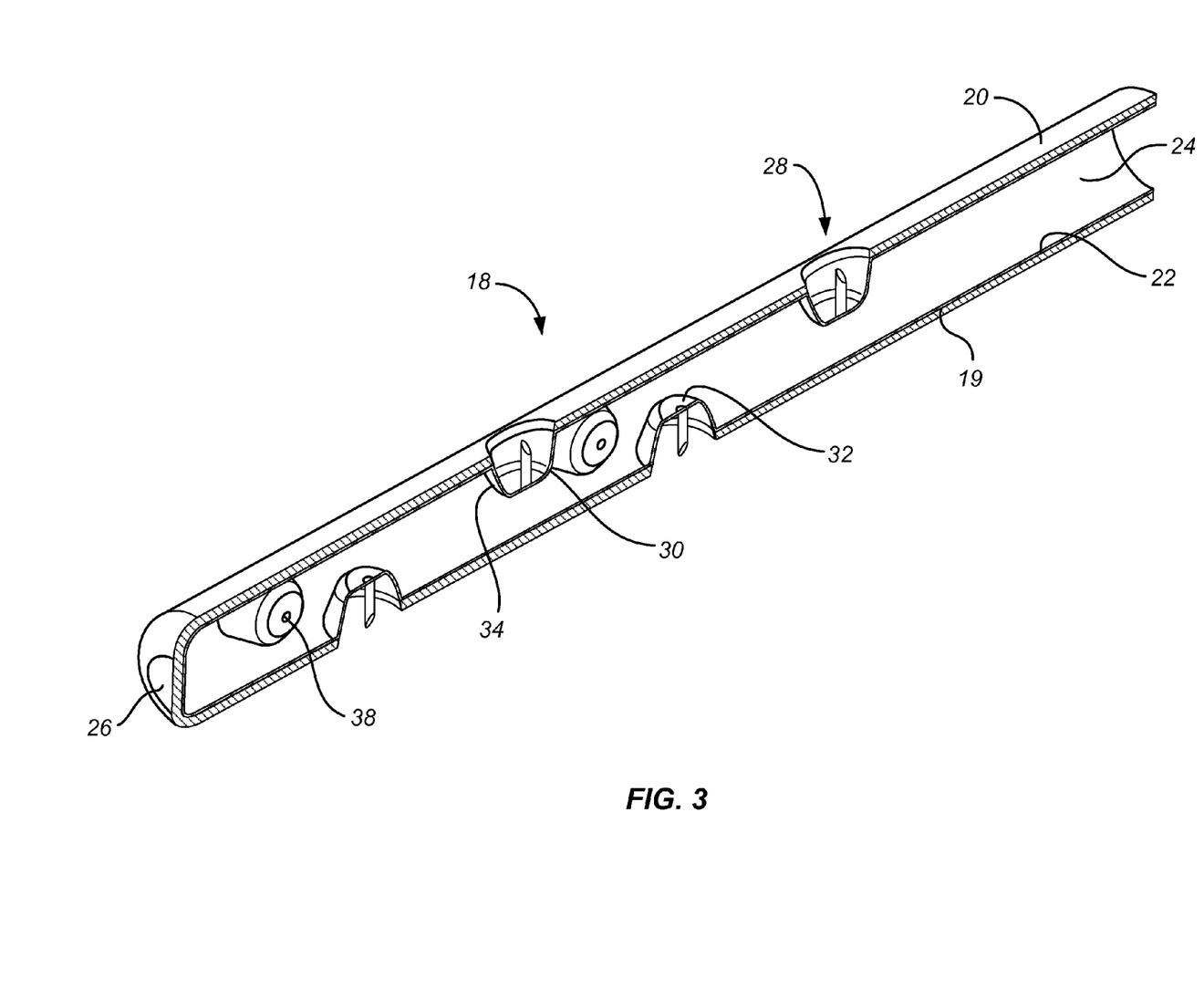
FIG. 3 is a cross-sectional view of the portion of the fluid delivery catheter of FIG. 2.

With reference to FIGS. 2 and 3, the treatment length 18 comprises an outer sleeve 20 and an inner lining 22. With reference to FIG. 3, the outer sleeve 20 comprises a tubular member defining a sleeve lumen 19 with a closed distal end 26. The sleeve 20 includes a sidewall having a plurality of spaced apertures 28. In the illustrated embodiment, the apertures 28 are circular, but in other embodiments the apertures 28 may define any shape.

Further, in the illustrated embodiment, the apertures 28 are spaced both along a longitudinal axis of the treatment length 18 and about a circumference of the treatment length 18. With reference to FIG. 2, the apertures 28 may trace a helix H about the treatment length 18, wherein each aperture 28 is spaced 90° circumferentially from each adjacent aperture 28 as measured along the longitudinal axis of the treatment length 18, and only one aperture 28 is positioned at any given point along the longitudinal axis of the treatment length 18. However, in alternative embodiments the apertures 28 could have any spacing. For example, a plurality of apertures 28 could be positioned at any given point along the longitudinal axis of the treatment length 18, with the plurality of apertures 28 spaced from one another about the circumference of the treatment length 18.

The outer sleeve 20 is preferably made of a material that is flexible and non-pressure-expandable, meaning that when a pressurized fluid is delivered to the interior of the outer sleeve 20 it will not expand appreciably as the pressure increases. As the pressure continues to increase toward the failure point of the outer sleeve 20, some expansion may occur as the outer sleeve 20 fails. However, such an outer sleeve 20 is still considered to be non-pressure-expandable. Example materials for the outer sleeve 20 include, without limitation, polymers such as polyurethanes in various durometers, polyether block amide (such as PEBAX®), thermoplastic polyurethane (TPU), polyethylene, or any other material.

With reference to FIGS. 2 and 3, the inner lining 22 comprises a tubular member defining a lining lumen 24. The lining 22 is received within the sleeve lumen 19 of outer sleeve 20, and includes a sidewall having a diameter such that the lining 22 abuts an inner surface of the sleeve lumen 19 along the entire treatment length 18. The lining 22 may extend the entire length of the elongate member 12 or only the length of the treatment length 18, or any portion thereof. The lining lumen 24 is generally aligned with the lumen of the elongate member 12 if the lining 22 is less than the full length of the elongate member 12. With reference to FIG. 3, the lining 22 includes a plurality of independently pressure-deformable portions 30 whose positions correspond to the apertures 28 in the outer sleeve 20. In the illustrated embodiment, each of the pressure-deformable portions 30 is shaped as a hollow conical frustum, open on one end, with a base 32 that is recessed within its respective aperture 28. In other embodiments, the pressure-deformable portions 30 may define any shape. A diameter of the base 32 is less than a diameter of its corresponding aperture 28, such that a sidewall 34 of each pressure-deformable portion 30 tapers inwardly from the aperture 28 to the base 32.

Figure 4:
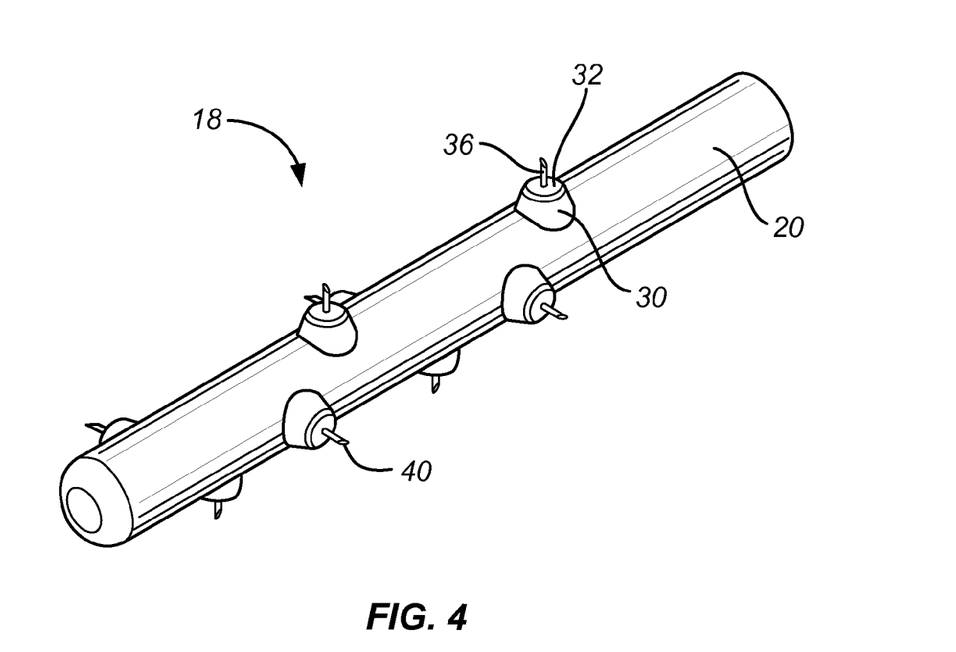
FIG. 4 is a detail view of the portion of the fluid delivery catheter of FIG. 1 indicated by the circle 1-1, showing the micro-needles in an extended position.
Figure 5:
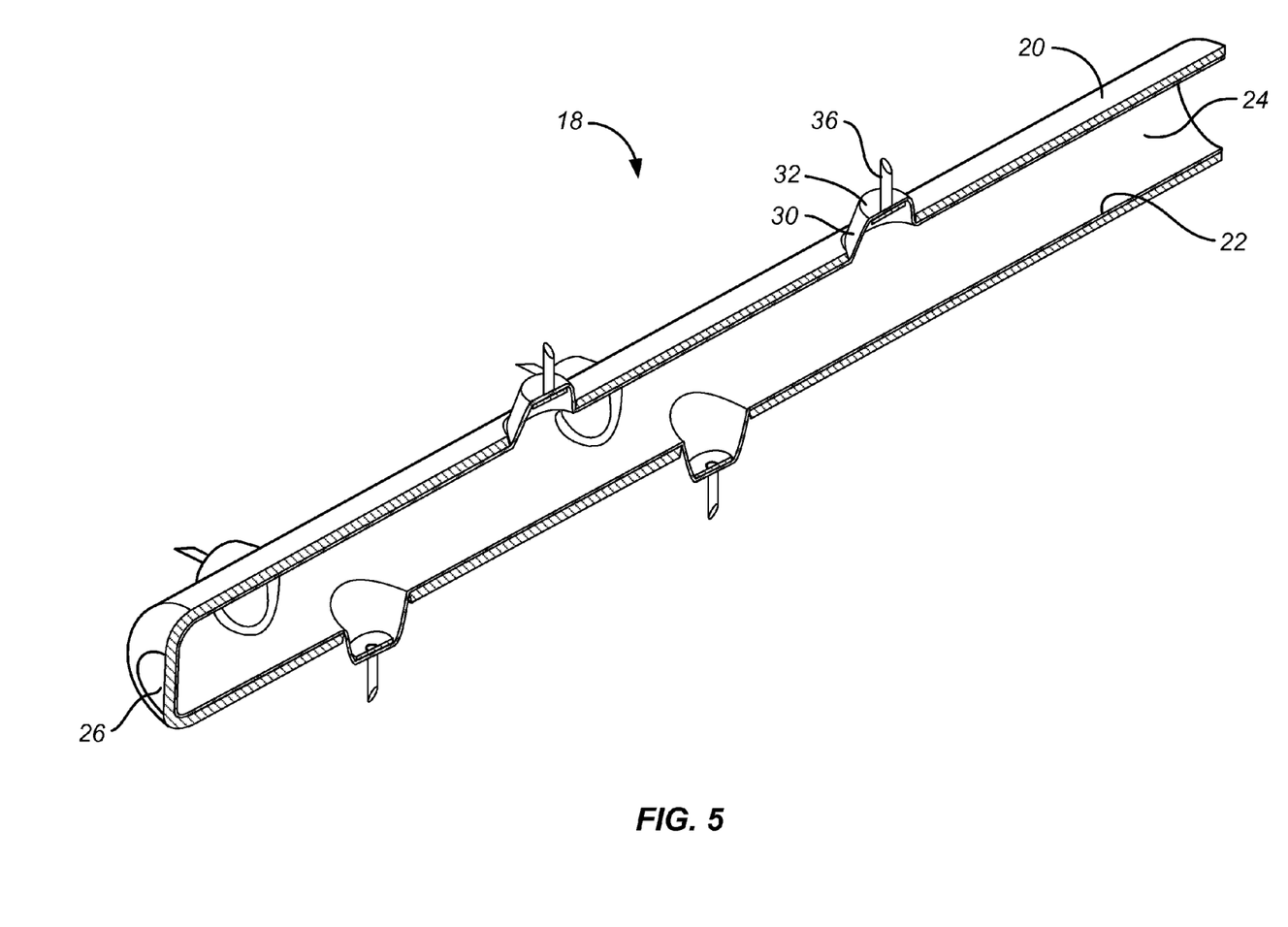
FIG. 5 is a cross-sectional view of the portion of the fluid delivery catheter of FIG. 4.

With reference to FIGS. 2-5, the pressure-deformable portions 30 are movable between a retracted position (FIGS. 2 and 3) and an extended position (FIGS. 4 and 5). The retracted position represents an at-rest configuration of the lining 22, which prevails when the pressure within the lining 22 is less than or equal to the ambient pressure. When a pressurized fluid is delivered into the lining lumen 24 of the lining 22, upon reaching a threshold pressure the pressure-deformable portions 30 "pop" radially outward to the extended position in which they protrude from the outer surface of the outer sleeve 20 (FIG. 4). In various embodiments, the threshold pressure may be in the range of 1-1,000 psi, such as 2-20 psi. The pressure-deformable portions 30 are further biased toward the retracted position, such that when the pressure within the lining 22 drops below the threshold pressure the pressure-deformable portions 30 "pop" radially inward to the retracted position.

The inner lining 22 is preferably made of a material that is flexible to enable movement between the retracted and extended positions, but elastomeric with a memory to facilitate inward biasing towards the retracted position. Example materials for the inner lining 22 include, without limitation, polymers such as polyurethanes in various durometers, or any other material.

With reference to FIGS. 4 and 5, the treatment length 18 further comprises a plurality of micro-needles 36. Each micro-needle 36 is secured to the base 32 of one of the pressure-deformable portions 30, with one micro-needle 36 per pressure-deformable portion 30. In one embodiment, the micro-needles 36 may be bonded or welded directly to each base 32. In another embodiment, with reference back to FIG. 3, an underside of each base 32 (on the interior side of the lining 22) may include an abutting needle anchor 38. Each needle anchor 38 may be a thin disk of a rigid or semi-rigid material. Each micro-needle 36 is embedded in a center of a corresponding one of the needle anchors 38, similar to a thumbtack, and extends through the base 32 of the corresponding one of the pressure-deformable portions 30. Each needle anchor 38 may be secured to its respective base 32 by any suitable means, such as with adhesive, ultrasonic welding, or laser spot welding. Each needle may be sized in length to penetrate into the target vessel. In other embodiments, each needle may be sized in length to penetrate beyond the target vessel to deliver fluid outside the target vessel. In still other embodiments, the length of the needles may be mixed to enable delivery of fluid both into and outside of the target vessel.

With reference to FIG. 4, each micro-needle 36 includes an internal needle lumen (not shown), and a sharp distal tip 40. The needle lumen is exposed at its proximal end (the end embedded in the needle anchor 38) so that the needle lumen is in fluid communication with the lining lumen 24 of the lining 22. Thus, when the pressurized fluid is introduced into the lining lumen 24, the pressurized fluid not only causes the pressure-deformable portions 30 to move to the extended position, but also the fluid to flow through the needle lumens and out the distal tips 40 of the micro-needles 36. The treatment length 18 can thus be used to inject a therapeutic fluid into a hollow anatomical structure (HAS) by introducing the therapeutic fluid into the lining lumen 24 under pressure, as described below. The needle lumens may be sized small enough to enable a build-up of pressure within the lining 22 to cause the pressure-deformable portions 30 to move to the extended position before significant amounts of the therapeutic fluid are delivered through the needle lumens. The internal diameter of the needle lumen may be balanced against the shape of the pressure-deformable portions 30 to calibrate the pressure necessary to move the pressure-deformable portions 30 to the extended position. For example, with the materials and material thickness being the same for both examples, the pressure-deformable portions 30A shown in FIG. 3A would require more pressure to move to the extended position that the pressure-deformable portions 30B shown in FIG. 3B.

Figure 3A:
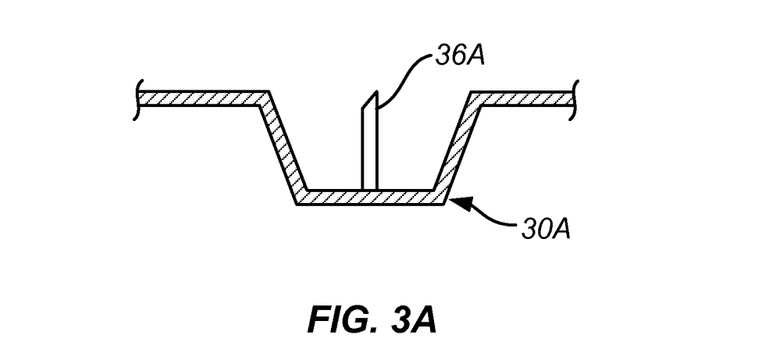
FIGS. 3A and 3B are cross-sectional views of alternative configurations for the fluid delivery catheter of FIG. 2.
Figure 3B:
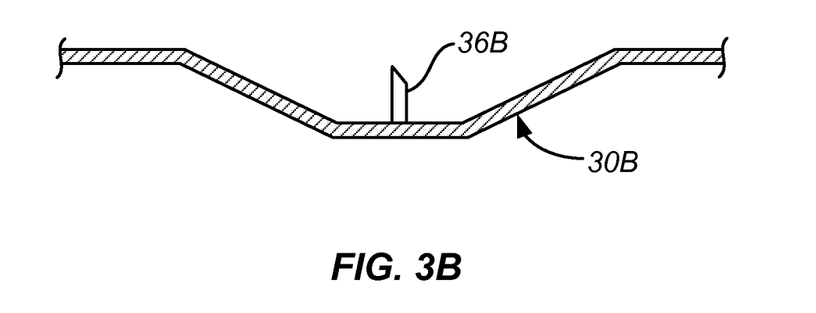

Thus, the needle 36A may have a needle lumen with a smaller internal diameter than the internal diameter of the needle lumen of the needle 36B to enable more pressure to build within the lining 22.

A method of using the present fluid delivery catheter 10 is illustrated with reference to FIGS. 6 and 7. An operator gains vascular access at an access site. For example, and without limitation, in a procedure such as denervation of the renal artery, the access site may be located along the femoral artery, and the access method may be percutaneous access. Before or after gaining access, the operator may flush or prime the lumen of the elongate member 12 and the lining lumen 24 with saline or the therapeutic fluid before putting the catheter 10 into the vasculature.

After gaining vascular access, the operator may advance the catheter 10 through the vasculature to the treatment site. The operator may use external imaging, such as ultrasound or fluoroscopy, to aid in guiding the catheter 10 to the treatment site. During the catheter 10 advancement phase, the catheter 10 is in the configuration of FIG. 3, with the micro-needles 36 retracted.

Figure 6:
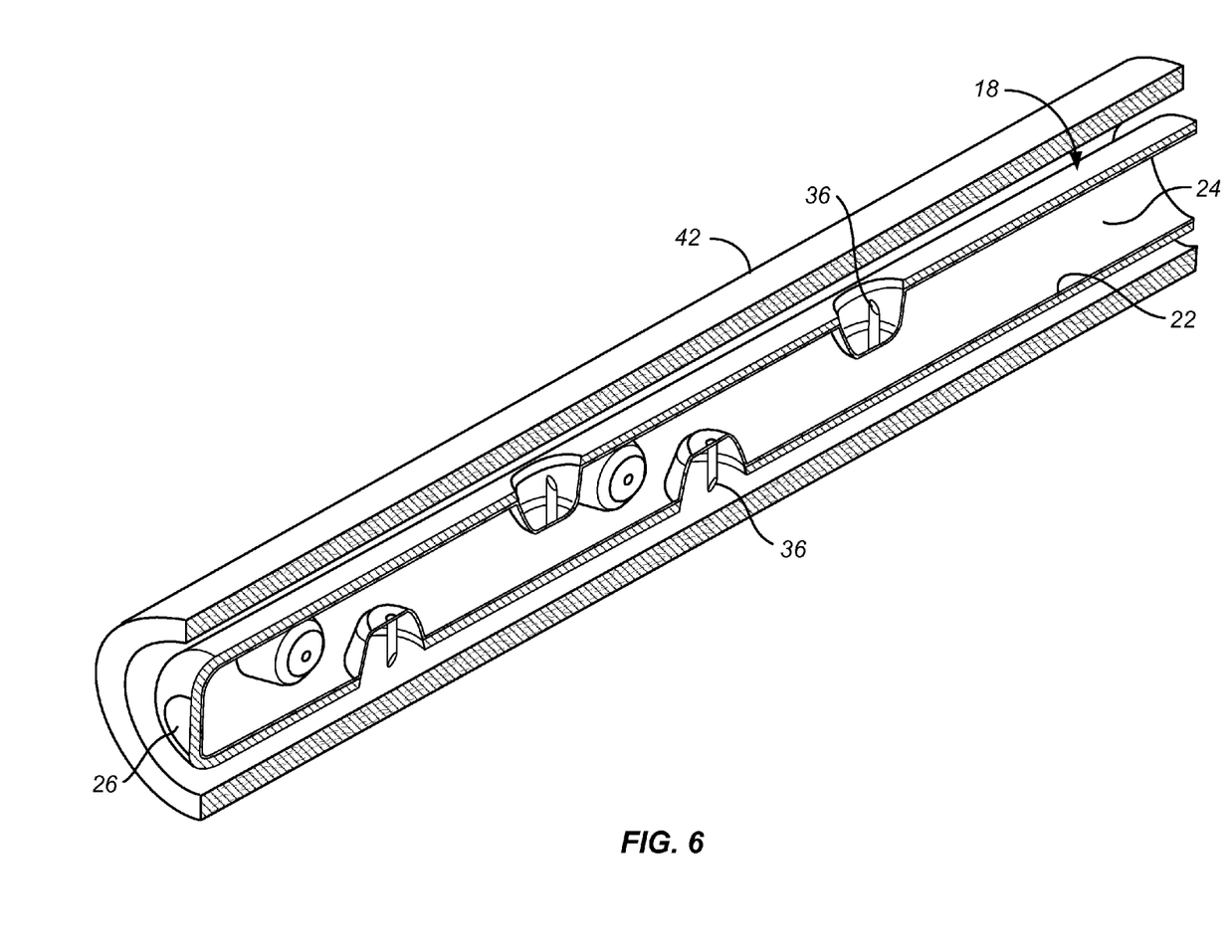
FIG. 6 is a detail view of the portion of the fluid delivery catheter of FIG. 3 positioned within a hollow anatomical structure.
Figure 7:
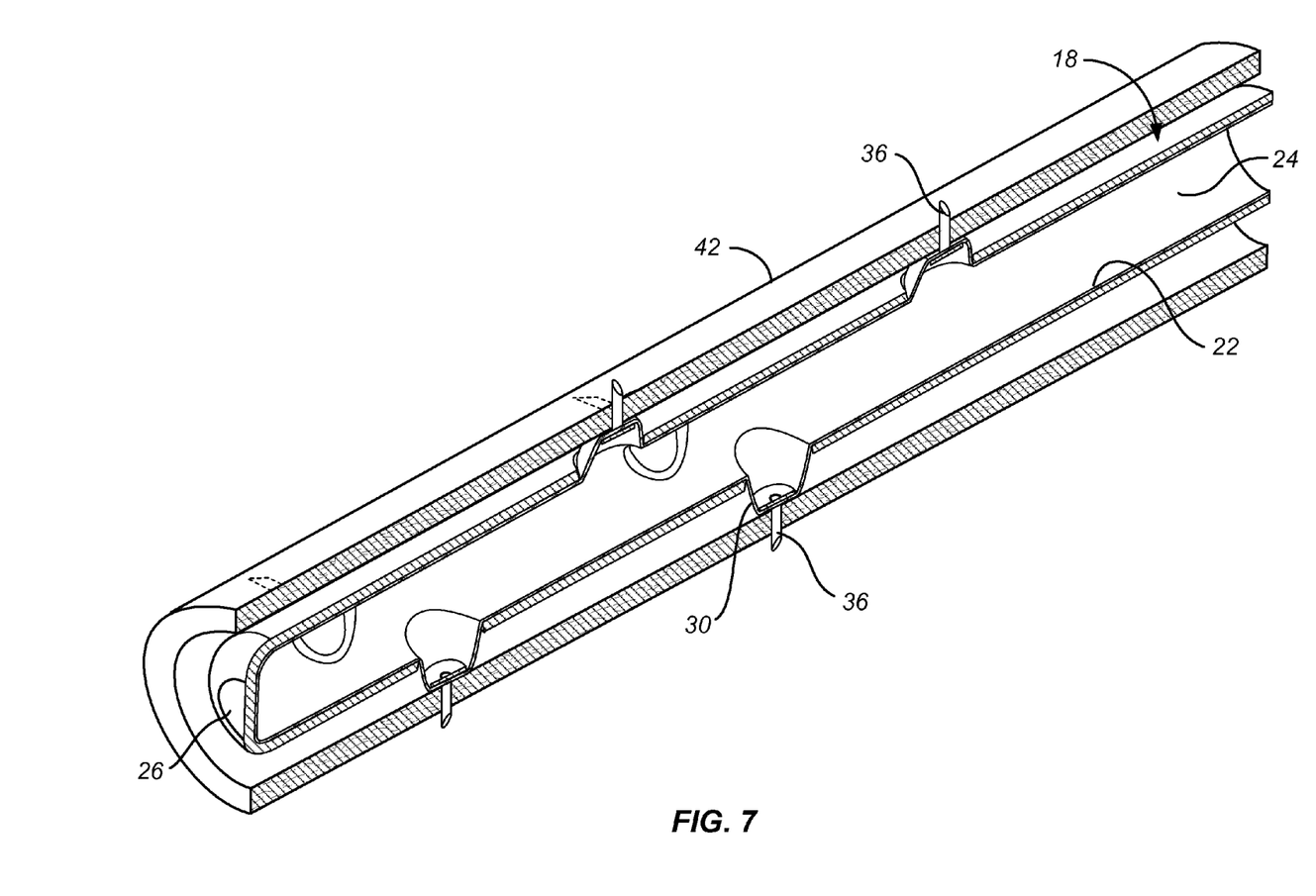
FIG. 7 is a detail view of the portion of the fluid delivery catheter of FIG. 5 positioned within a hollow anatomical structure.

With reference to FIG. 6, after the treatment length 18 has reached the treatment site and is in the desired position within the vessel 42, the operator connects a source of therapeutic fluid to the female coupler 16 at the proximal end 14 of the catheter 10 (FIG. 1). The source of therapeutic fluid may be, for example, a syringe. The operator then injects the therapeutic fluid through the elongate member 12 and into the lining lumen 24 of the inner lining 22. The therapeutic fluid may be any liquid or gas that may be injected into or around a vessel to produce an effect on the vessel or surrounding tissue, such as tumescent fluid, sclerosant agents, medicants or drugs. As fluid pressure builds within the lining lumen 24, upon reaching a threshold pressure the pressure-deformable portions 30 "pop" radially outward to the extended position, causing the micro-needles 36 to penetrate the wall of the vessel 42, as shown in FIG. 7. As fluid continues to flow distally through the lining lumen 24 of the inner lining 22, it flows outward through the micro-needles 36, thus delivering the therapeutic fluid to the treatment site. In some embodiments in which the lining lumen 24 is flushed with the therapeutic fluid prior to being inserted into the vasculature, the injection fluid of the foregoing step may comprise saline or some other benign fluid.

In certain embodiments, the operator may inject tumescent anesthesia at the treatment site prior to delivering the therapeutic fluid into the lining lumen 24. The tumescent anesthesia compresses the vessel 42 at the treatment site to facilitate penetration of the vessel wall by the micro-needles 36 when the therapeutic fluid is injected into the lining lumen 24. Other methods of compressing the vessel 42, such as externally applied manual compression, may also be used in addition to, or instead of, tumescent anesthesia.

When the desired amount of therapeutic fluid has been delivered, the operator ceases injecting fluid. As fluid pressure within the lumen 24 drops, upon reaching the threshold pressure, the pressure-deformable portions 30 "pop" radially inward to the retracted position due to their radially inward bias, as shown in FIG. 6. The operator subsequently withdraws the catheter 10 from the vessel 42 and concludes the treatment procedure by closing the access site.

As illustrated above, embodiments of the present fluid delivery catheter 10 advantageously enable efficient and simultaneous delivery of fluid therapy from within a vessel to areas just outside the vessel wall via multiple targeted delivery areas. The longitudinal and circumferential spacing of the micro-needles 36 enables wide dispersal of the therapeutic fluid both along and around the vessel, thereby covering a large treatment area in as little as one injection of therapeutic fluid without any need to translate or rotate the catheter 10 during the procedure.

Figure 8:
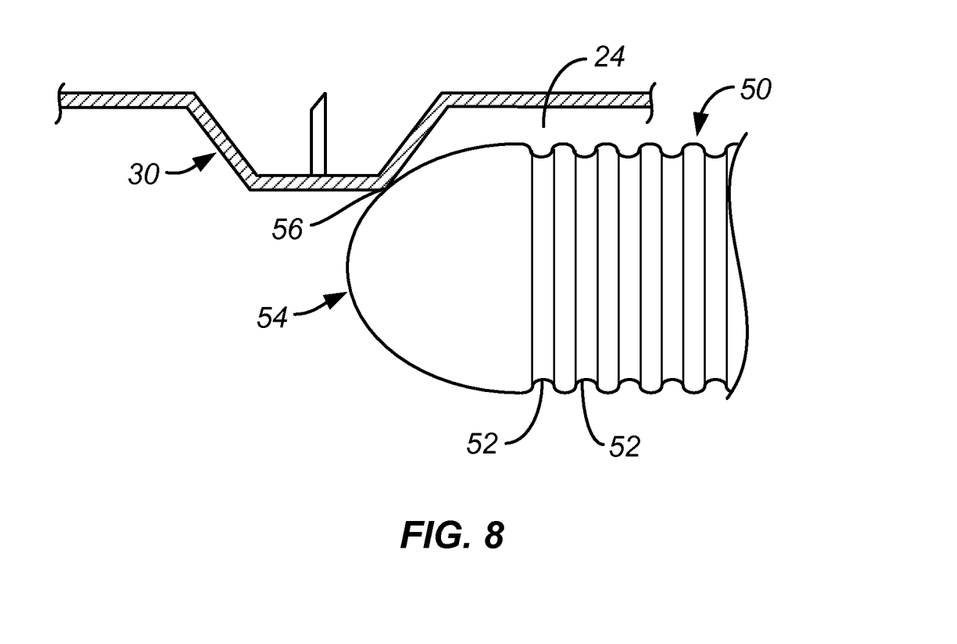
FIGS. 8 and 9 are cross-sectional views of an alternative technique for deploying the micro-needles of the fluid delivery catheter of FIG. 2.
Figure 9:
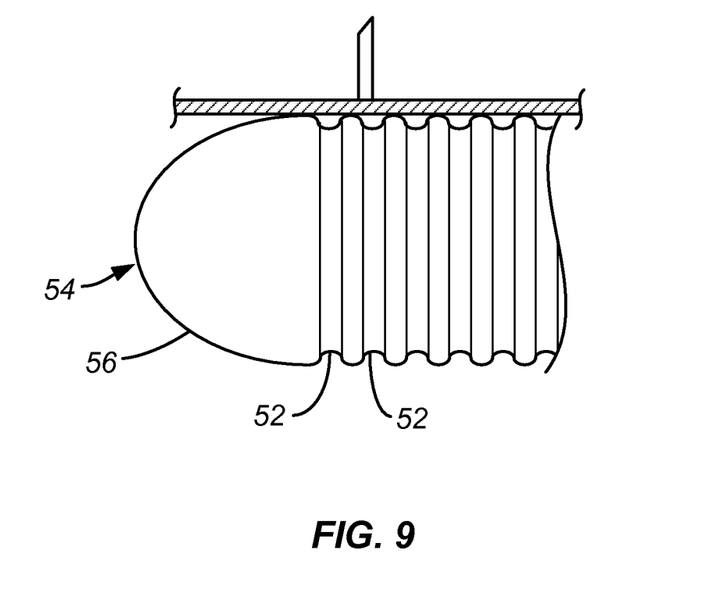

In an alternative embodiment, the pressure-deformable portions may be moved to the extended position by a flexible wire advanced into and through the elongate member and into engagement with the pressure-deformable portions. Referring to FIGS. 8 and 9, an elongate wire 50 may include annular grooves 52 to enable fluid flow through the lumen of the elongate member 12 and the lining lumen 24. The annular grooves 52 are configured to also enable fluid communication between the therapeutic fluid in the lining lumen 24 and needle lumens. The annular grooves 52 may be a plurality of individual circumferential grooves, or may be helically wound along the length, or a portion of the length, of the elongate wire 50. As shown in FIG. 8, a distal end 54 of the wire 50 engages the deformable portions 30 as the wire 50 is advanced along the lining lumen 24. The distal end 54 of the wire 50 is configured to enable smooth engagement with the deformable portions 30, such as a rounded end or ramp 56. As the wire 50 is advanced further distally, the wire 50 pushes the deformable portion 30 to the extended position (FIG. 9). Therapeutic fluid may then be injected into the elongate member 12, along the lumen of the elongate member, and into the lining lumen 24, where the fluid may then pass out the needle lumens. When the procedure is completed, the wire 50 is retracted proximally, and the deformable portions 30 will return to the retracted position automatically due to inward bias of the deformable portions 30. The wire 50 has the benefit of enabling the needles 36 to have a larger needle lumen for the delivery of more fluid quickly because the fluid is not required to build the pressure in the lining 24 to move the deformable portions 30.

In another example embodiment, the wire 50 may have longitudinal grooves or flutes along the length of the wire 50. The longitudinal grooves, like the annular grooves 52, enable fluid flow around the wire and into the needle lumens.

It is to be understood that the foregoing description is intended to illustrate and not limit the scope of the invention, which is defined by the scope of the appended claims. Other embodiments are within the scope of the following claims.

What is claimed is:

1. An apparatus for delivery of a fluid at a treatment site, the apparatus comprising:
    an elongate catheter;
    a non-pressure-expandable outer sleeve defining a treatment length at or near a distal end of the catheter, the outer sleeve defining a plurality of spaced apertures and an outer sleeve lumen;
    a flexible inner lining disposed within the outer sleeve lumen and defining a plurality of independently pressure-deformable portions and a lining lumen, wherein each of the plurality of pressure deformable portions is biased radially inward and is generally aligned with one of the plurality of spaced apertures;
    a plurality of micro-needles secured to the pressure-deformable portions and in fluid communication with the lining lumen,
    wherein the pressure-deformable portions and the micro-needles are recessed beneath an outer surface of the outer sleeve in an at-rest configuration, and the pressure-deformable portions are deformable to an extended position in which at least a portion of the micro-needles protrude above the outer surface of the outer sleeve, and a flexible wire configured to engage with the deformable portions as the flexible wire is axially advanced into the lining lumen so as to move at least one of the deformable portions from the at-rest configuration to the extended position, the flexible wire being further configured to allow passage of a fluid through the lining lumen and into the deformable portions when the flexible wire is advanced into the lining lumen.

2. The apparatus of claim 1, wherein the pressure-deformable portions are spaced from one another along a longitudinal axis of the treatment length and about a circumference of the treatment length.

3. The apparatus of claim 2, wherein positions of the pressure-deformable portions trace a helix about the treatment length.

4. The apparatus of claim 1, wherein each of the pressure-deformable portions is shaped as a conical frustum.

5. The apparatus of claim 4, wherein each of the micro-needles is secured to a base of each of the frustums.

6. The apparatus of claim 1, wherein the pressure-deformable portions are deformed to the extended position by an elongate wire, the elongate wire comprising at least one of annular grooves or longitudinal grooves.

7. The apparatus of claim 1, wherein a distal end of the catheter is closed.

8. An apparatus for delivery of a fluid at a treatment site, the apparatus comprising:
   an elongate catheter;
   a non-pressure-expandable outer sleeve defining a treatment length at or near a distal end of the catheter, the outer sleeve defining a plurality of spaced apertures and an outer sleeve lumen;
   a flexible inner lining disposed within the outer sleeve lumen and defining a plurality of independently pressure-deformable portions and a lining lumen, wherein each of the plurality of pressure deformable portions is shaped as a conical frustum that is biased radially inward and positioned to generally align with one of the plurality of spaced apertures;
   a plurality of micro-needles secured to a base of the frustum of the pressure-deformable portions and in fluid communication with the lining lumen,
   wherein the pressure-deformable portions and the micro-needles are recessed beneath an outer surface of the outer sleeve in an at-rest configuration, and the pressure-deformable portions are deformable to an extended position in which at least a portion of the micro-needles protrude above the outer surface of the outer sleeve, further comprising a flexible wire configured to engage with the deformable portions as the flexible wire is axially advanced into the lining lumen so as to move at least one of the deformable portions from the at-rest configuration to the extended position, the flexible wire being further configured to allow passage of a fluid through the lining lumen and into the deformable portions when the flexible wire is advanced into the lining lumen.

9. The method of claim 8, wherein the pressure-deformable portions are deformed to the extended position by an elongate wire, the elongate wire comprising at least one of annular grooves or longitudinal grooves.

* * * * *